United States Patent
Iwabuchi et al.

(10) Patent No.: US 7,396,960 B2
(45) Date of Patent: Jul. 8, 2008

(54) SULFONIUM SALTS

(75) Inventors: Jun Iwabuchi, Chiba (JP); Yosuke Osawa, Chiba (JP)

(73) Assignee: Toyo Gosei Co., Ltd., Chiba (JP)

( * ) Notice: Subject to any disclaimer, the term of this patent is extended or adjusted under 35 U.S.C. 154(b) by 0 days.

(21) Appl. No.: 11/724,221

(22) Filed: Mar. 15, 2007

(65) Prior Publication Data

US 2007/0219368 A1  Sep. 20, 2007

(30) Foreign Application Priority Data

Mar. 16, 2006 (JP) ............................. 2006-073441
Dec. 28, 2006 (JP) ............................. 2006-355579

(51) Int. Cl.
*C07D 285/00* (2006.01)
*C07C 319/00* (2006.01)

(52) U.S. Cl. ......................................... 568/18; 568/45

(58) Field of Classification Search ................... 568/18, 568/45
See application file for complete search history.

(56) References Cited

U.S. PATENT DOCUMENTS 4,491,628 A    1/1985  Ito et al. ..................... 430/176
6,395,450 B1 *  5/2002  Park et al. ................. 430/270.1

* cited by examiner

*Primary Examiner*—Kahsay T Habte
(74) *Attorney, Agent, or Firm*—Young & Thompson

(57) ABSTRACT

The present invention provides a sulfonium salt which can serve as a photo-acid-generator, the sulfonium salt not raising the problem of poor compatibility to a photoresist polymer having an acid-dissociable group. The sulfonium salt is represented by formula (1):

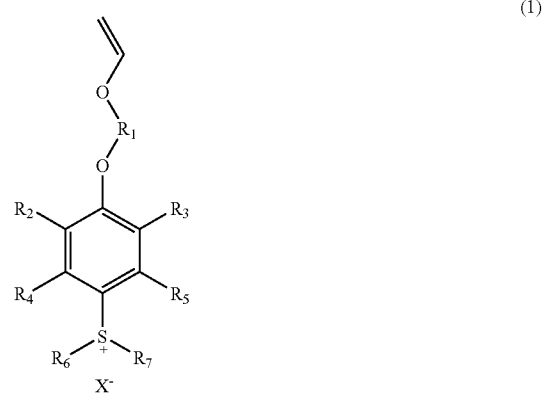

(1)

wherein $R_1$ represents a linear or branched C2 to C9 divalent hydrocarbon group; each of $R_2$ to $R_5$ represents a hydrogen atom or a linear or branched C1 to C3 hydrocarbon group; each of $R_6$ and $R_7$ represents an organic group; $R_6$ and $R_7$ may be linked together to form a divalent organic group; and $X^-$ represents an anion.

1 Claim, No Drawings

SULFONIUM SALTS

The entire disclosure of Japanese Patent Applications Nos. 2006-073441 filed Mar. 16, 2006 and 2006-355579 filed Dec. 28, 2006 is expressly incorporated by reference herein.

BACKGROUND OF THE INVENTION

1. Field of the Invention

The present invention relates to a sulfonium salt useful for a photo-acid-generator (i.e., a chemical agent for generating an acid through irradiation), which is readily decomposed through irradiation with an actinic ray such as a deep UV ray, an electron beam, an X-ray, or an EUV (extreme UV ray), particularly for a photo-acid-generator for use in chemically amplified photoresist material.

2. Description of the Related Art

In the field of semiconductor devices such as large-scale integrated circuit devices, typically DRAMs, there is keen demand for further enhancement in density, integration, and operational speed. In order to satisfy the demand, in industrial production of electronic devices, a more rigorous level of half-micron-scale microprocessing technique; e.g., photolithographic technique for micro-patterning, is required. In micro-patterning through photolithography, enhancement in resolution (R) is a key factor. The resolution can be enhanced by employing an actinic ray (exposure light) having a shorter wavelength λ in patterning the resist material, since resolution (R) of a demagnification stepper is calculated by Rayleigh's formula: R=k·λ/NA (wherein λ represents the wavelength of exposure light, NA represents numerical aperture, and k represents a process factor).

Regarding photoresists, U.S. Pat. No. 4,491,628 and other documents disclose chemically amplified photoresists as those suitable for exposure light of short wavelength. A characteristic feature of chemically amplified photoresist is that a photo-acid-generator contained in such a resist generates protonic acid through irradiation with light, and the generated protonic acid catalytically reacts with a resist resin or other components of the photoresist when the photoresist is heated after completion of exposure. Most photoresists currently in use are of the chemically amplified type.

Meanwhile, a variety of sulfonium salts are known to serve as a photo-acid-generator for chemically amplified photoresists. However, such conventional photo-acid-generators have drawbacks; for example, poor compatibility to a photoresist polymer having an acid-dissociable group; i.e., a group dissociated or decomposed by acid. Needless to say, when a photoresist containing such a photo-acid-generator is patternwise exposed to an actinic ray, the obtained pattern has unsatisfactory shape characteristics, which is problematic.

SUMMARY OF THE INVENTION

Under such circumstances, an object of the present invention is to provide a sulfonium salt which can serve as a photo-acid-generator, the sulfonium salt not raising the problem of poor compatibility to a photoresist polymer having an acid-dissociable group.

Accordingly, a first mode of the present invention provides a sulfonium salt represented by formula (1):

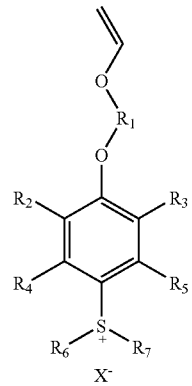

(1)

wherein $R_1$ represents a linear or branched C2 to C9 divalent hydrocarbon group; each of $R_2$ to $R_5$ represents a hydrogen atom or a linear or branched C1 to C3 hydrocarbon group; each of $R_6$ and $R_7$ represents an organic group; $R_6$ and $R_7$ may be linked together to form a divalent organic group; and $X^-$ represents an anion.

In a second mode of the present invention, which is directed to a specific embodiment of the sulfoium salt of the first mode, the anion $X^-$ is an anion represented by formula (2):

$$C_kH_mF_nSO_3^- \quad (2)$$

wherein each of k, m, and n is an integer of $\geq 0$; when m is 0, k is an integer of 1 to 8, n is 2k+1, and formula (2) represents a perfluoroalkylsulfonate ion; when n is 0, k is an integer of 1 to 15, m is an integer of $\geq 1$, and formula (2) represents an alkylsulfonate ion, a benzenesulfonate ion, or an alkylbenzenesulfonate ion; and when each of m and n is an integer of $\geq 1$, k is an integer of 1 to 10, and formula (2) represents a fluorinated benzenesulfonate ion, a fluorinated alkylbenzenesulfonate ion, or a fluorinated alkylsulfonate ion.

In a third mode of the present invention, which is directed to a specific embodiment of the sulfoium salt of the first mode, the anion $X^-$ is a bis(perfuloroalkylsulfon)imide ion represented by formula (3):

$$(C_pF_{2p+1}SO_2)_2N^- \quad (3)$$

wherein p represents an integer of 1 to 8.

In a fourth mode of the present invention, which is directed to a specific embodiment of the sulfoium salt of the first mode, the anion $X^-$ is an anion represented by formula (4).

(4)

In a fifth mode of the present invention, which is directed to a specific embodiment of the sulfoium salt of the first mode, the anion $X^-$ is $Cl^-$, $Br^-$, $I^-$, $BF_4^-$, $AsF_6^-$, $SbF_6^-$, or $PF_6^-$.

In a sixth mode of the present invention, which is directed to a specific embodiment of the sulfoium salt of any one of the first to fifth modes, the sulfonium salt is an acid generator.

The sulfonium salt of the present invention effectively decomposes through irradiation with an actinic ray (e.g., a deep UV ray, an electron beam, an X-ray, or an EUV), to thereby serve as a photo-acid-generator. In addition, since the sulfonium salt has a structure which can be incorporated into a polymer having an acid-dissociable group, the polymer and the acid generator can be used as a single species. Therefore, the problem involved in a conventional sulfonium salt serving as a photo-acid-generator, which is used in combination with a photosensitive polymer; i.e., poor compatibility to the photosensitive polymer, can be solved.

DETAILED DESCRIPTION OF PREFERRED EMBODIMENTS

The present invention will next be described in detail.

The sulfonium salt of the present invention is a compound represented by formula (1), wherein $R_1$ represents a C2 to C9 divalent hydrocarbon group which may be linear or branched; each of $R_2$ to $R_5$ represents a hydrogen atom or a linear or branched C1 to C3 hydrocarbon group; and each of $R_6$ and $R_7$ represents an organic group. Examples of the organic group include linear, branched, or alicyclic alkyl groups carbocyclic aryl groups, and heterocyclic aryl groups. The organic group is preferably a carbocyclic aryl group, with phenyl, methylphenyl, and t-butylphenyl being particularly preferred. The carbocyclic aryl groups and heterocyclic aryl groups may have a substituent having 1 to 30 carbon atoms. The C1 to C30 substituent is preferably a C1 to C30 hydrocarbon group or alkoxy group. Examples of the C1 to C30 hydrocarbon group serving as the substituent include alkyl groups such as methyl, ethyl, propyl, isopropyl, n-butyl, sec-butyl, t-butyl, pentyl, hexyl, heptyl, octyl, t-amyl, decanyl, dodecanyl, and hexadecanyl; alicyclic alkyl groups such as cyclopropyl, cyclopentyl, cyclohexyl, cyclooctyl, cyclododecanyl, cyclohexadecanyl, and adamantyl; and aryl groups such as phenyl and naphthyl. Examples of the C1 to C30 alkoxy group serving as the substituent include methoxy, ethoxy, propoxy, isopropoxy, n-butoxy, isobutoxy, sec-butoxy, t-butoxy, pentyloxy, t-amyloxy, n-hexyloxy, n-octyloxy, n-dodecyloxy, and 1-adamantyloxy.

$R_6$ and $R_7$ may be linked together to form a ring. In this case, the formed ring is a divalent organic group having the aforementioned carbon skeleton; i.e., —$R_6$—$R_7$—. Examples of such a divalent group include C3 to C9 alicyclic alkyl groups in which $R_6$ and $R_7$ are linked together to form a saturated carbon skeleton. Examples of preferred alicyclic alkyl groups include polymethylene groups such as tetramethylene and pentamethylene. When the divalent organic group —$R_6$—$R_7$— forms a ring with S, the formed ring is preferably 4- to 8-membered ring, more preferably 5- to 6-membered ring.

In formula (1), no particular limitation is imposed on the species of the anion $X^-$, and an anion conventionally employed in photo-acid-generators may be employed. Examples of the anion include anions represented by formula (2); anions represented by formula (3); the anion represented by formula (4) (cyclo-1,3-perfluoropropanedisulfonimdo ion); halide ions such as $Cl^-$, $Br^-$, and $I^-$; and inorganic anions, e.g. fluoride anions such as $BF_4^-$ (tetrafluoroborate ion), $AsF_6^-$ (hexafluoroarsenate ion), $SbF_6^-$ (hexafluoroantimonate ion), or $PF_6^-$ (hexafluorophosphate ion).

In formula (2), each of k, m, and n is an integer of $\geqq 0$; when m is 0, k is an integer of 1 to 8, n is 2k+1, and formula (2) represents a perfluoroalkylsulfonate ion. Examples of preferred perfluoroalkylsulfonate ions include $CF_3SO_3^-$ (trifluoromethanesulfonate ion), $C_4F_9SO_3^-$ (nonafluorobutanesulfonate ion), and $C_8F_{17}SO_3^-$ (heptadecafluorooctanesulfonate ion).

In formula (2), when n is 0, k is an integer of 1 to 15, m is an integer of $\geqq 1$, and formula (2) represents an alkylsulfonate ion, a benzenesulfonate ion, or an alkylbenzenesulfonate ion. In the case of alkylsulfonate ions, m is represented by 2k+1. Examples of preferred alkylsulfonate ions include $CH_3SO_3^-$ (methanesulfonate ion), $C_2H_5SO_3^-$ (ethanesulfonate ion), $C_9H_{19}SO_3^-$ (1-nonanesulfonate ion), and cross-linked ring alkylsulfonate ions such as 10-camphorsulfonate ion. Examples of preferred alkylbenzenesulfonate ions include 4-methylbenzenesulfonate ion and 2,4,6-triisopropylbenzenesulfonate ion.

In formula (2), when each of m and n is an integer of $\geqq 1$, k is an integer of 1 to 10, and formula (2) represents a fluorinated benzenesulfonate ion, a fluorinated alkylbenzenesulfonate ion, or a fluorinated alkylsulfonate ion. Examples of preferred fluorinated benzenesulfonate ions include 2-fluorobenzenesulfonate ion, 4-fluorobenzenesulfonate ion, 2,4-difluorobenzenesulfonate ion, and pentafluorobenzenesulfonate ion. Examples of preferred fluorinated alkylbenzenesulfonate ions include 2-trifluoromethylbenzenesulfonate ion, 4-trifluoromethylbenzenesulfonate ion, 2,4-bis(trifluoromethyl)benzenesulfonate ion, and 3,5-bis(trifluoromethyl)benzenesulfonate ion. Examples of preferred fluorinated alkylsulfonate ions include 1,1,2,3,3,3-hexafluoropropanesulonate ion.

The anion represented by formula (3) is bis(perfluoroalkylsulfon)imide ion (wherein p is an integer of 1 to 8). Examples of preferred bis(perfluoroalkylsulfon)imide ions include bis(trifluoromethylsulfon)imide ion and bis(pentafluoroethylsulfon)imide ion.

Since the aforementioned sulfonium salt of the present invention effectively decomposes through irradiation with an actinic ray (e.g., a deep UV ray, an electron beam, an X-ray, or an EUV), the sulfonium salt serves as a photo-acid-generator. In addition, the sulfonium salt has a structure which can be incorporated into a polymer having an acid-dissociable group. Thus, when the sulfonium salt of the present invention is employed as a single species with the polymer, a photoresist composition can be successfully produced, while the problem involved in conventional sulfonium salt serving as a photo-acid-generator, which is used in combination with a photosensitive polymer; i.e., poor compatibility to the photosensitive polymer can be solved.

Next, an exemplary method for producing a sulfonium salt of the prsent invention will be described. Firstly, as shown in the following scheme, a compound represented by formula (5) is reacted with dialkyl sulfoxide in methanesulfonic acid ($CH_3SO_3H$) in the presence of phosphorus pentoxide ($P_2O_5$) as a catalyst, to thereby produce a compound (methanesulfonate salt) represented by formula (6). Dialkyl sulfoxide can be readily produced through oxidation of dialkyl sulfide with hydrogen peroxide.

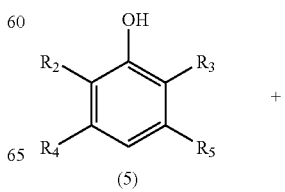

(5)

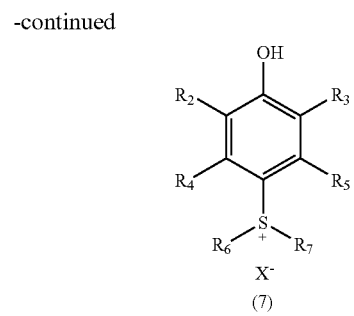

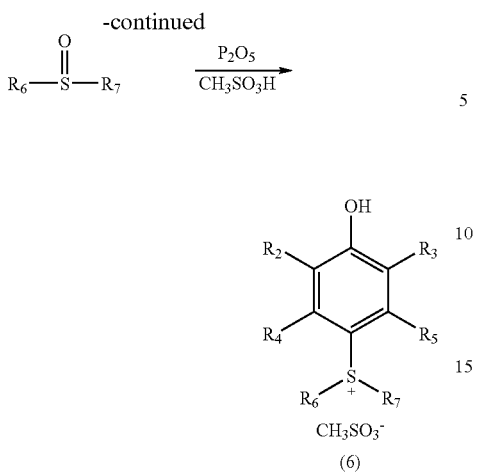

Phosphorus pentoxide serving as a catalyst is used in an amount of 0.1 to 3.0 mol with respect to 1 mol of the compound represented by formula (5), preferably 0.5 to 1.5 mol. Methanesulfonic acid is used in an amount of 1 to 10 mol with respect to 1 mol of the compound represented by formula (5), preferably 4 to 6 mol. The reaction is generally performed at 0 to 50° C. for 1 to 15 hours, preferably 10 to 30° C. for 3 to 8 hours. The reaction is terminated by adding water to the reaction system.

Subsequently, as shown in the following scheme, $CH_3SO_3^-$ of the compound represented by formula (6) is converted to $X^-$ through salt exchange. In the reaction scheme, $M^+$ represents a monovalent metal ion. Specifically, an acid $H^+X^-$ or salt $M^+X^-$ ($X^-$ including anions represented by the aforementioned formula (2), (3), or (4)) is added to an aqueous solution of the compound represented by formula (6) in an amount of 1 to 2 mol with respect to 1 mol of the compound represented by formula (6), preferably 1.05 to 1.2 mol. The reaction solvent is preferably a chlorine-containing solvent such as dichloromethane or chloroform. The reaction is generally performed at 10 to 50° C., preferably 20 to 30° C. After completion of reaction, the aqueous layer is separated from the reaction system, and the organic layer is washed with water. After washing, crystallization is performed by use of an appropriate solvent, to thereby yield a compound represented by formula (7). Alternatively, after formation of the compound represented by formula (6), potassium iodide may be added to the reaction solution for salt exchange, whereby the compound represented by formula (6) in the form of iodide salt is isolated. After purification of the iodide salt, further salt exchange with $X^-$ or sulfonate ester may be performed.

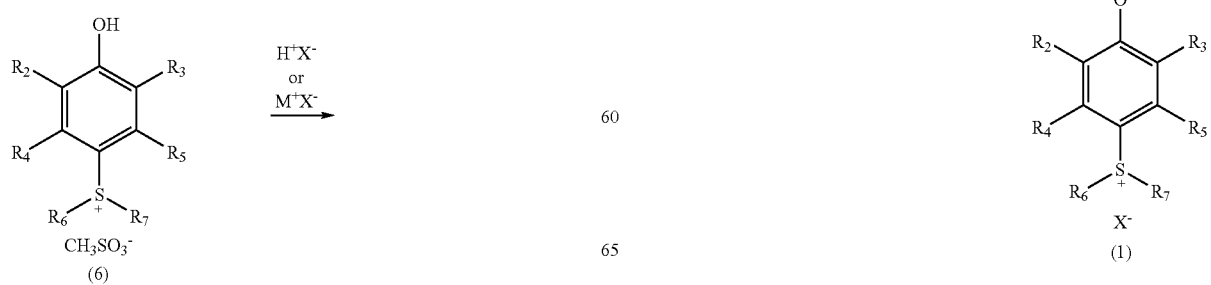

Subsequently, as shown in the following scheme, de-hydrohalide reaction between the compound represented by formula (7) and the compound represented by formula (8) is performed, to thereby produce a sulfonium salt represented by formula (1). In the reaction scheme, Y represents a halogen atom such as Cl or Br. Specifically, the compound represented by formula (7) is reacted with the compound represented by formula (8) in, for example, a polar solvent in the presence of a basic catalyst such as potassium carbonate ($K_2CO_3$). The reaction is generally performed at 60 to 90° C. After completion of reaction, water is added to the reaction system, and the formed aqueous layer is washed with a non-polar solvent such as hexane, followed by extraction with a chlorine-containing solvent. The formed organic layer is removed and washed with water, followed removal of the chlorine-containing solvent, to thereby yield the sulfonium salt represented by formula (1). Notably, the compounds (5) to (8) employed in the above reactions may be commercial products.

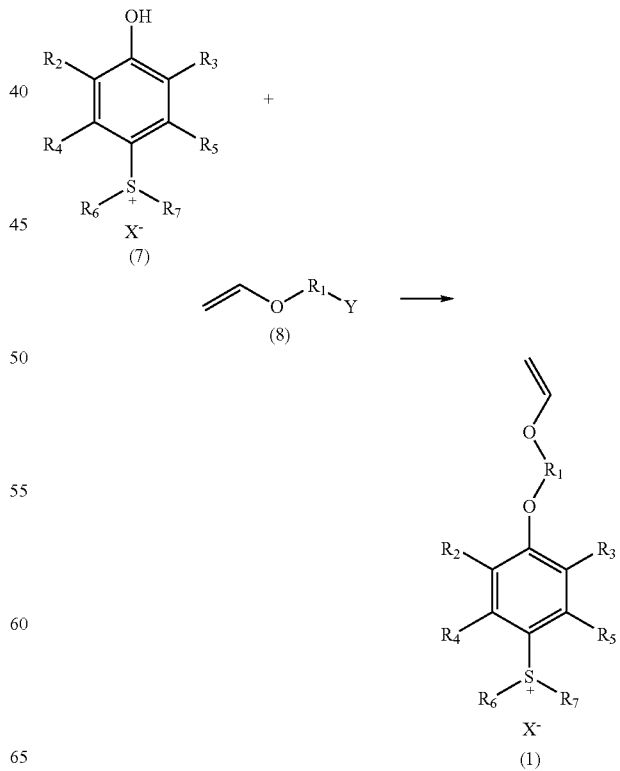

The present invention will next be described in detail by way of examples, which should not be construed as limiting the invention thereto.

Example 1

Synthesis of 4-vinyloxyethoxyphenyldiphenylsulfonium perfluorobutanesulfonate salt

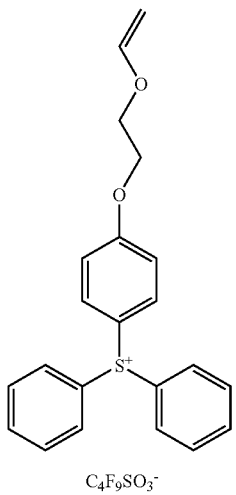

$C_4F_9SO_3^-$

Example 2

Synthesis of 4-vinyloxyethoxy-3,5-dimethylphenyl-diphenylsulfonium perfluorobutanesulfonate salt $C_4F_9SO_3^-$ 4-Hydroxyphenyldiphenylsulfonium perfluorobutanesulfonate salt (52.2 g), potassium carbonate (18.0 g), and N,N,N',N'-tetramethylethylenediamine (1.05 g) were dissolved in dimethyl sulfoxide (26.1 g). Chloroethyl vinyl ether (13.9 g) was added to the solution, followed by heating to 80° C. The reaction mixture was stirred for 15 hours and cooled to 30° C. or lower. After removal of solid through filtration, water (100 g) was added to the filtrate, and the aqueous layer was washed three times with hexane (100 g). To the washed aqueous layer, dichloromethane (209 g) and water (260 g) were added under stirring, whereby the target substance was extracted to the dichloromethane layer. The organic layer was repeatedly washed with distilled water until the pH of the separated aqueous layer was shifted to 7. The solvent was removed by means of a rotary evaporator, to thereby yield 69.9 g of an oily substance. Through $^1$H-NMR and ion chromatography, the substance was identified to be 4-vinyloxyethoxyphenyldiphenylsulfonium perfluorobutanesulfonate salt.

$^1$H-NMR (400 MHz, CDCl$_3$) δ 4.05-4.08 (m, 3H), 4.24 (d, J=7.4, 2.4 Hz, 1H), 4.31-4.33 (m, 2H), 6.49 (dd, J=14.4, 7.4 Hz, 1H), 7.24 (d, J=6.8 Hz, 2H), 7.64-7.74 (m, 12H)

4-Hydroxy-3,5-dimethylphenyldiphenylsulfonium perfluorobutanesulfonate salt (56.1 g), potassium carbonate (18.4 g), and N,N,N',N'-tetramethylethylenediamine (1.07 g) were dissolved in dimethyl sulfoxide (118 g). Chloroethyl vinyl ether (14.2 g) was added to the solution, followed by heating to 80° C. The reaction mixture was stirred for 47 hours and cooled to 30° C. or lower. After removal of solid through filtration, water (280 g) was added to the filtrate, and the aqueous layer was washed three times with hexane (168 g). To the washed aqueous layer, dichloromethane (226 g) and water (50 g) were added under stirring, whereby the target substance was extracted to the dichloromethane layer. The organic layer was repeatedly washed with distilled water until the pH of the separated aqueous layer was shifted to 7. The solvent was removed by means of a rotary evaporator, to thereby yield 41.0 g of an oily substance. Through $^1$H-NMR and ion chromatography, the substance was identified to be 4-vinyloxyethoxy-3,5-dimethylphenyldiphenylsulfonium perfluorobutanesulfonate salt.

$^1$H-NMR (400 MHz, CDCl$_3$) δ 2.35 (s, 6H), 4.02-4.07 (m, 3H), 4.13-4.15 (m, 2H), 4.24 (dd, J=14.2, 2.4 Hz, 1H), 6.51 (dd, J=14.2, 6.8 Hz, 1H), 7.37 (s, 2H), 7.69-7.78 (m, 10H)

Example 3

Synthesis of 4-vinyloxyethoxyphenyldi(4-t-butylphenyl)sulfonium perfluorobutanesulfonate salt

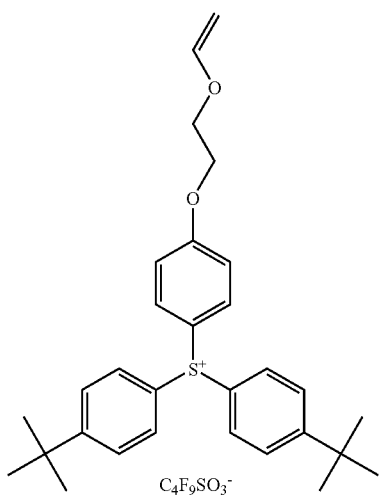

4-Hydroxyphenyldi(4-t-butylphenyl)sulfonium perfluorobutanesulfonate salt (28.4 g), potassium carbonate (8.56 g), and N,N,N',N'-tetramethylethylenediamine (0.50 g) were dissolved in dimethyl sulfoxide (143 g). Chloroethyl vinyl ether (6.30 g) was added to the solution, followed by heating to 80° C. The reaction mixture was stirred for 15 hours and cooled to 30° C. or lower. After removal of solid through filtration, water (220 g) and dichloromethane (113 g) were added to the filtrate, whereby the target substance was extracted to the dichloromethane layer. The organic layer was repeatedly washed with distilled water until the pH of the separated aqueous layer was shifted to 7. The solvent was removed by means of a rotary evaporator, and the formed oily substance was dissolved in acetonitrile (100 g). The acetonitrile layer was washed five times with hexane (85 g). The solvent was removed by means of a rotary evaporator, to thereby yield 24.5 g of a brown oily substance. Through $^1$H-NMR and ion chromatography, the substance was identified to be 4-vinyloxyethoxyphenyldi(4-t-butylphenyl)sulfonium perfluorobutanesulfonate salt.

$^1$H-NMR (400 MHz, CDCl$_3$) δ 1.33 (s, 18H), 4.05-4.0 (m, 3H), 4.24 (dd, J=14.3, 2.4 Hz, 1H), 4.32-4.34 (m, 2H), 6.50 (dd, J=14.3, 6.8 Hz, 1H), 7.23-7.28 (m, 2H), 7.58-7.71 (m, 10H)

Example 4

Synthesis of 4-vinyloxyethoxy-3,5-dimethylphenyldi(4-t-butylphenyl)sulfonium perfluorobutanesulfonate salt

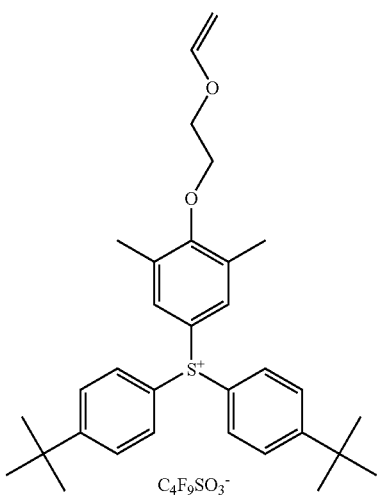

4-Hydroxy-3,5-dimethylphenyldi(4-t-butylphenyl)sulfonium perfluorobutanesulfonate salt (28.6 g), potassium carbonate (8.10 g), and N,N,N',N'-tetramethylethylenediamine (0.46 g) were dissolved in dimethyl sulfoxide (142 g). Chloroethyl vinyl ether (6.08 g) was added to the solution, followed by heating to 80° C. The reaction mixture was stirred for 19 hours and cooled to 30° C. or lower. After removal of solid through filtration, water (20.9 g) was added to the filtrate, and the aqueous layer was washed three times with hexane (85.1 g). To the washed aqueous layer, dichloromethane (226 g) and water (141 g) were added under stirring, whereby the target substance was extracted to the dichloromethane layer. The organic layer was repeatedly washed with distilled water until the pH of the separated aqueous layer was shifted to 7. The solvent was removed by means of a rotary evaporator, to thereby yield 27.4 g of a brown oily substance. Through $^1$H-NMR and ion chromatography, the substance was identified to be 4-vinyloxyethoxy-3,5-dimethylphenyldi(4-t-butylphenyl)sulfonium perfluorobutanesulfonate salt.

$^1$H-NMR (400 MHz, CDCl$_3$) δ 1.35 (s, 18H), 2.36 (s, 6H), 4.02-4.08 (m, 3H), 4.12-4.14 (m, 2H), 4.25 (d, J=14.3, 6.1 Hz, 1H), 6.50 (dd, J=14.3, 6.6 Hz, 1H), 7.35 (s, 2H), 7.59-7.75 (m, 8H)

Example 5

Synthesis of 4-vinyloxyoctoxyphenyldiphenylsulfonium perfluorobutanesulfonate salt

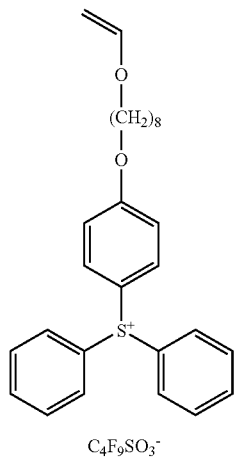

8-Chloro-1-octanol (1.23 g), sodium carbonate (0.47 g), di-μ-chlorobis[η-cyclootcadieneiridium(I)] (0.47 g), and vinyl acetate (1.31 g) were added to toluene (6.15 g), and the mixture was stirred at 100° C. for four hours. After cooling of the mixture to room temperature, the solvent was removed. The product was purified through column chromatography employing a hexane-dichloromethane (2:1 by vol.) mixture as a solvent, to thereby yield 1.16 g of 8-chlorooctyl vinyl ether as a colorless liquid.

4-Hydroxyphenyldiphenylsulfonium perfluorobutanesulfonate salt (2.67 g), potassium carbonate (0.78 g), and N,N,N',N'-tetramethylethylenediamine (0.05 g) were dissolved in dimethyl sulfoxide (13.3 g). 8-Chlorooctyl vinyl ether (1.05 g) was added to the solution, followed by heating to 80° C. The reaction mixture was stirred for 18 hours and cooled to 30° C. or lower. After removal of solid through filtration, water (13.3 g) was added to the filtrate, and the aqueous layer was washed three times with hexane (7.96 g). To the washed aqueous layer, dichloromethane (10.6 g) and water (14 g) were added under stirring, whereby the target substance was extracted to the dichloromethane layer. The organic layer was repeatedly washed with distilled water until the pH of the separated aqueous layer was shifted to 7. The solvent was removed by means of a rotary evaporator, to thereby yield 2.53 g of a brown oily substance. Through $^1$H-NMR and ion chromatography, the substance was identified to be 4-vinyloxyoctoxyphenyldiphenylsulfonium perfluorobutanesulfonate salt.

$^1$H-NMR (400 MHz, CDCl$_3$) δ 1.36-1.47 (m, 8H), 1.64-1.67 (m, 2H), 1.78-1.83(m, 2H), 3.67 (t, J=6.6 Hz, 2H), 3.96 (dd, J=6.8, 2.0 Hz, 1H), 4.04 (t, J=6.6 Hz, 2H). 4.16(dd, J=14.4, 2.0 Hz, 1H), 6.46 (dd, J=14.4, 6.8 Hz, 1H), 7.16-7.19 (m, 2H), 7.65-7.76 (m, 12H)

Example 6

Synthesis of 4-vinyloxyethoxyphenyldiphenylsulfonium cyclo(1,3-perfluoropropanedisulfon)imide salt

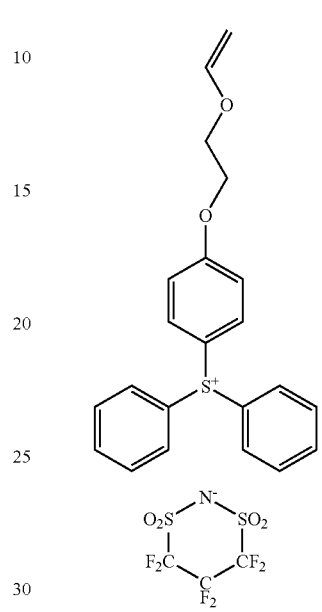

Phosphorus pentoxide (4.66 g) and diphenyl sulfoxide (13.3 g) were dissolved in methanesulfonic acid (63.1 g), and phenol (9.26 g) was added to the solution, followed by stirring at room temperature for 15 hours. While the mixture was maintained at 30° C. or lower, water (199 g) was added dropwise thereto. The thus-obtained aqueous layer was washed three times with t-butyl methyl ether (66.4 g), and dichloromethane (120 g) and cyclo-1,3-perfluoropropanedisulfonimide potassium salt (23.9 g) were added to the washed aqueous layer, followed by stirring for two hours. After termination of stirring, the formed aqueous layer was removed, and a 0.1 wt. % aqueous ammonia (66.4 g) was added to the organic layer, followed by stirring. Subsequently, the organic layer was repeatedly washed with distilled water until the pH of the separated aqueous layer was shifted to 7. The solvent was removed by means of a rotary evaporator, to thereby yield 32.1 g of 4-hydroxyphenyldiphenylsulfonium cyclo(1,3-perfluoropropanedisulfon)imide salt as an oily substance.

4-Hydroxyphenyldiphenylsulfonium cyclo(1,3-perfluoropropanedisulfon)imide salt (32.1 g), potassium carbonate (11.2 g), and N,N,N',N'-tetramethylethylenediamine (0.67 g) were dissolved in dimethyl sulfoxide (164 g). Chloroethyl vinyl ether (8.65 g) was added to the solution, followed by heating to 80° C. The reaction mixture was stirred for 15 hours and cooled to 30° C. or lower. After removal of solid through filtration, water (80 g) was added to the filtrate, and the aqueous layer was washed three times with hexane (40 g). To the washed aqueous layer, dichloromethane (120 g) and water (260 g) were added under stirring, whereby the target substance was extracted to the dichloromethane layer. The organic layer was repeatedly washed with distilled water until the pH of the separated aqueous layer was shifted to 7. The solvent was removed by means of a rotary evaporator, to thereby yield 29.1 g of an oily substance. Through $^1$H-NMR and ion chromatography, the substance was identified to be 4-vinyloxyethoxyphenyldiphenylsulfonium cyclo(1,3-perfluoropropanedisulfon)imide salt.

$^1$H-NMR (400 MHz, CDCl$_3$) δ 4.05-4.08 (m, 3H), 4.24 (d, J=7.4, 2.4 Hz, 1H), 4.31-4.33 (m, 2H), 6.49 (dd, J=14.4, 7.4 Hz, 1H), 7.24 (d, J=6.8 Hz, 2H), 7.64-7.74 (m, 12H)

Example 7

Synthesis of 4-vinyloxyethoxyphenyldi(4-t-butylphenyl)sulfonium 2,4,6-triisopropylbenzenesulfonate salt

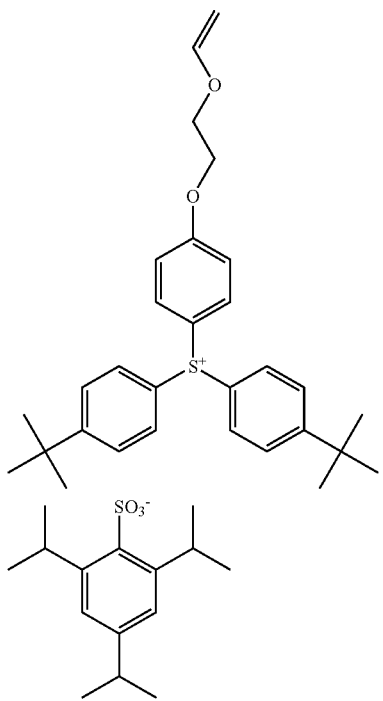

4-Hydroxyphenyldi(4-t-butylphenyl)sulfonium 2,4,6-triisopropylbenzenesulfonate salt (5.00 g), potassium carbonate (1.28 g), and N,N,N',N'-tetramethylethylenediamine (0.10 g) were dissolved in dimethyl sulfoxide (15 g). Chloroethyl vinyl ether (0.83 g) was added to the solution, followed by heating to 80° C. The reaction mixture was stirred for 15 hours and cooled to 30° C. or lower. After removal of solid through filtration, water (75 g) and dichloromethane (44 g) were added to the filtrate, whereby the target substance was extracted to the dichloromethane layer. The organic layer was repeatedly washed with distilled water until the pH of the separated aqueous layer was shifted to 7. The solvent was removed by means of a rotary evaporator, to thereby yield 4.64 g of a brown oily substance. Through $^1$H-NMR and ion chromatography, the substance was identified to be 4-vinyloxyethoxyphenyldi(4-t-butylphenyl)sulfonium 2,4,6-triisopropylbenzenesulfonate salt.

$^1$H-NMR (400 MHz, CDCl$_3$) δ 1.21 (d, J=6.8 Hz, 18H), 1.32 (s, 18H), 2.83 (sep, J=6.8 Hz, 1H), 4.02-4.08 (m, 3H), 4.24 (dd, J=14.3, 2.4 Hz, 1H), 4.29-4.31 (m, 2H), 4.73 (sep, J=6.8 Hz, 2H), 6.50 (dd, J=14.4, 6.8 Hz, 1H), 7.02 (s, 2H), 7.24-7.26 (m, 2H), 7.60-7.89 (m, 10H)

Application Example 1

Production of Photosensitive Polymer:

Polyhydroxystyrene (20.0 g) (Mw=16,400, Mw/Mn=1.09) was dissolved in 1,3-dioxolane (147 mL) under nitrogen. After dissolution, 1,3-dioxolane was removed until the water content of the system was reduced to 100 ppm. The thus-obtained reaction mixture was cooled to 20° C., and 35 wt. % hydrochloric acid (25.0 μL) was added thereto. A sulfonate salt of the present invention (4-vinyloxyethoxyphenyldiphenylsulfonium perfluorobutanesulfonate salt) produced in Example 1 was dissolved in 1,3-dioxolan so that the concentration was adjusted to 56.2 wt. %, and the solution (5.70 g) was added dropwise to the above mixture over 30 minutes, followed by stirring at 30° C. for four hours. The thus-obtained solution was neutralized with 4-dimethylaminopyridine, and the product was added dropwise to pure water (667 g), to thereby precipitate a solid. The solid was separated through filtration and dissolved again in 1,3-dioxolane for re-precipitation. The precipitates were dried at 35° C. for 24 hours, to thereby yield 22.8 g of a polymer. Through $^1$H-NMR, the polymer was identified to be a photosensitive polymer in which 15.8% of the hydroxyl groups of polyhydroxystyrene were substituted by a structure derived from the aforementioned sulfonate salt of the invention.

Preparation and Characteristics Evaluation of Photoresist

The photosensitive polymer produced in Application Example 1 (100 parts by weight) and triethanolamine (0.24 parts by weight) were dissolved in propylene glycol monomethyl acetate (525 parts by weight), and the solution was filtered by means of a PTFE filter, to thereby prepare a liquid positive-type photoresist. The resist was applied onto a silicon wafer (diameter: 4 inches) by means of a spinner, and pre-baked at 110° C. for 90 seconds, to thereby form a resist film having a thickness of 500 nm. The resist film was irradiated with light from a xenon lamp (wavelength: 248 nm), and post-baked at 110° C. for 90 seconds. Subsequently, breakthrough time of the resist film was determined at 23° C. by use of a developer (2.38 wt. % tetramethylammonium hydroxide aqueous solution). Herein, "breakthrough time" is a time (sec) required for complete dissolution, through development, of the resist film cured by irradiation at a predetermined energy.

In the above analysis, the breakthrough time was determined to 12 seconds (100 mJ) and 3 seconds (500 mJ). This indicates that solubility of the photosensitive polymer produced in Application Example 1 in the developer was changed from "virtually insoluble" to "soluble," since the acid-dissociable moiety of the polymer was dissociated by the acid which was generated from a structure intrinsic to the sulfonium salt of the present invention through irradiation with light from the xenon lamp.

Application Examples 2 to 7

Instead of the sulfonium salt produced in Example 1, photosensitive polymers 2 to 7 were produced from sulfonium salts produced in Examples 2 to 7, respectively, in a manner similar to that of Application Example 1. Similar to Application Example 1, liquid positive-type photoresists were prepared from respective photosensitive polymers, and the corresponding resist films were formed. In a similar manner, light exposure, post-baking, development, and determination of breakthrough time were carried out.

Polymers 2 to 7 were found to exhibit a breakthrough time of 12±2 seconds (100 mJ) and a 3±1 seconds (500 mJ). This indicates that solubility of the photosensitive polymers 2 to 7 in the developer was changed from "virtually insoluble" to "soluble," since the acid-dissociable moieties of the polymers were dissociated by the acid which was generated from structures intrinsic to the sulfonium salts of the present invention through irradiation with light from the xenon lamp.

What is claimed is:

1. A sulfonium salt represented by formula (1):

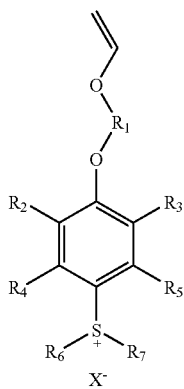

(1)

wherein $R_1$ represents a linear or branched C2 to C9 divalent hydrocarbon group; each of $R_2$ to $R_5$ represents a hydrogen atom or a linear or branched C1 to C3 hydrocarbon group; each of $R_6$ and $R_7$ represents a phenyl group or a phenyl group which has a substituent having a C1 to C30 alkyl group, or $R_6$ and $R_7$ together with S atom to which they are attached form a heterocyclic ring with a saturated carbon of C3 to C9 alkyl groups; and $X^-$ is an anion which is represented by formula (2), or represented by formula (3) which is a bis(perfluoroalkylsulfon)imide ion, or $Cl^-$, $Br^-$, $I^-$, $BF_4^-$, $AsF_6^-$, $SbF_6^-$, or $PF_6^-$, $$C_kH_mF_nSO_3^- \qquad (2)$$

wherein each of k, m, and n is an integer of $\geq 0$; when m is 0, k is an integer of 1 to 8, n is 2k+1, and formula (2) represents a perfluoroalkylsulfonate ion; when n is 0, k is an integer of 1 to 15, m is an integer of $\geq 1$, and formula (2) represents an alkylsulfonate ion, a benzenesulfonate ion, or an alkylbenzenesulfonate ion; and when each of m and n is an integer of $\geq 1$, k is an integer of 1 to 10, and formula (2) represents a fluorinated benzenesulfonate ion, a fluorinated alkylbenzenesulfonate ion, or a fluorinated alkylsulfonate ion, $$(C_pF_{2p+1}SO_2)_2N^- \qquad (3)$$

wherein p represents an integer of 1 to 8.

* * * * *